United States Patent
Su et al.

(10) Patent No.: US 9,687,438 B2
(45) Date of Patent: Jun. 27, 2017

(54) METHOD FOR ENHANCING COLLAGEN SECRETION AND PREVENTING CUTANEOUS AGING USING CHENOPODIUM FORMOSANUM EXTRACT

(71) Applicant: TCI Co., Ltd., Taipei (TW)

(72) Inventors: Hsiang-Ling Su, Taipei (TW); Chin-Hsiu Yu, Taipei (TW); Ying-Ju Chen, Taipei (TW)

(73) Assignee: TCI Co., Ltd., Taipei (TW)

( * ) Notice: Subject to any disclaimer, the term of this patent is extended or adjusted under 35 U.S.C. 154(b) by 25 days.

(21) Appl. No.: 14/636,561

(22) Filed: Mar. 3, 2015

(65) Prior Publication Data

US 2015/0265527 A1    Sep. 24, 2015

(30) Foreign Application Priority Data

Mar. 20, 2014    (TW) .............................. 103110528 A (51) Int. Cl.
*A61K 8/97*    (2017.01)
*A61Q 19/08*    (2006.01)

(52) U.S. Cl.
CPC ................ *A61K 8/97* (2013.01); *A61Q 19/08* (2013.01); *A61K 2800/522* (2013.01); *A61K 2800/92* (2013.01)

(58) Field of Classification Search
None
See application file for complete search history.

(56) References Cited

U.S. PATENT DOCUMENTS

2010/0330239 A1*   12/2010   Tsai et al. ..................... 426/250

FOREIGN PATENT DOCUMENTS

TW    201102107 A1 *   1/2011
TW    201102108 A1 *   1/2011

* cited by examiner

*Primary Examiner* — Susan Hoffman
(74) *Attorney, Agent, or Firm* — WPAT, P.C., Intellectual Property Attorneys; Anthony King (57) ABSTRACT

Provided is a method for enhancing collagen secretion and preventing cutaneous aging using *Chenopodium formosanum* extract. The *Chenopodium formosanum* extract includes active ingredients that are able to effectively enhance the ability of collagen secretion of dermal fibroblasts as well as prevent the glycation of collagen and resist the damage of ultraviolet light exposure. The preparation of the *Chenopodium formosanum* extract is environmental friendly and is able to promote the economic value of *Chenopodium formosanum*; thus, the present invention is suitable for applications in the development of food products, especially beverages, skin care and cosmetic products.

14 Claims, 10 Drawing Sheets

METHOD FOR ENHANCING COLLAGEN SECRETION AND PREVENTING CUTANEOUS AGING USING CHENOPODIUM FORMOSANUM EXTRACT

CROSS-REFERENCES TO RELATED APPLICATIONS

This application claims the priority of Taiwan Patent Application No. 103110528 filed on 20 Mar. 2014, which is incorporated herewith by reference.

BACKGROUND OF THE INVENTION

1. Field of the Invention

The present invention is related to a method of using *Chenopodium formosanum* extract. In particular, the present invention is related to the method for enhancing collagen secretion and preventing cutaneous aging using *Chenopodium formosanum* extract, which can effectively enhance collagen secretion rate, prevent glycation of collagen, and resist ultraviolet light damage.

2. The Prior Arts

*Chenopodium formosanum*, commonly known as Formosa lambsquarters, Taiwan quinoa, or Djuli, is a unique annual or perennial herbaceous plant with good drought and salt tolerant abilities found in the mountainous region of low to middle elevation in Taiwan. *Chenopodium formosanum* is edible, wherein the use of the plantlets, shoots, leaves, and spikes thereof are found in recipe, while the dehulled seeds thereof, in particular, can be grinded into flour and mixed with water to make food products such as rice balls and dumplings. *Chenopodium formosanum* is rich in protein and dietary fiber, therefore, is anti-oxidative. Moreover, *Chenopodium formosanum* is a popular flavor additive used by aboriginals in Taiwan during the process of brewing liquor. As for traditional Chinese medicine, *Chenopodium formosanum* is mild and moderate, and can be beneficial regarding the treatment of fever, diarrhea, abscess, and itching skin. Hence, *Chenopodium formosanum* is often regarded as "the ruby of cereals" due to its wide uses and advantages set forth hereinbefore.

Collagen is a biological macromolecule and the most abundant protein found in vertebrates. For humans, collagen takes up to one-third of the total protein. Collagen is mostly presented in the extracellular matrix of connective tissues and serves as intercellular scaffolds. Collagen is found in cartilages, corneas, vascular walls, and internal organs. In particular, collagen is found in skin and provides support to the skin cells in order to maintain the tightness and flexibility of skin. Current researches indicate that, apart from aging and accumulation of damages caused by environmental factors that lead to the decrease of collagen secretion and synthesis by dermal fibroblasts, glycation is also a major cause for the depredation of collagen in skin. When the rate of lost of collagen is greater than its rate of synthesis, wrinkles and loosening would appear on the skin accordingly.

Glycation refers to the chemical reaction in which glucose is attached to protein and promotes protein molecules to aggregate and interconnect. Once glycated, the flexibility of collagen would be lost, and the fibrous glycated collagen become easily accumulated, which accelerates the wrinkle formation on skin. Some researches revealed that in hyperglycemia, the carbonyl group of the glucose in blood would bind directly to the arginine or lysine of protein, nucleic acid, or lipid during glycation. The entire glycation process is known as Maillard Reaction and would give a final product called advanced glycation end-product (AGE). The accumulation of AGEs not only results in cutaneous aging but also angiosclerosis. Besides, AGEs exhibit neurotoxicity and would damage nerve cells and lead to neuron-associated diseases such as Alzheimer's disease.

Thus, collagen supplement or method for enhancing the secretion of collagen of cells is critical regarding prevention or amelioration of cutaneous aging. Moreover, preventing the glycation of collagen can not only maintain the flexibility and tightness of skin but also preclude diseases caused by accumulation of glycated protein. Collagen-related products now available in the market are mainly collagen supplements; however, when directly applied to skin, it is almost impossible for the collagen supplements to penetrate stratum corneum and reach the dermal fibroblasts in dermis due to the large molecular size of collagen. Although injecting collagen can immediately reduce the amount of wrinkles on skin, it is complex and costly since regular administration is required. The injected collagen is likely to be digested by enzymes in the body. On the other hand, when the collagen supplement is taken orally, upon reaching the gastrointestinal track, the helix structure of the collagen would soon be digested into polypeptides then into smaller molecules and finally into amino acids by different digestive enzymes. These amino acids can be utilized to build proteins but not exclusively collagen, therefore, the effect of collagen supplement via oral administration is limited.

In light of above, enhancing the secretion of collagen of the human dermal fibroblasts is more effective regarding the production and utilization of collagen comparing to collagen supplements. Furthermore, preventing the glycation of collagen can retain the flexibility of collagen and, hence, maintain skin tightness. In addition, the amelioration of cutaneous aging can be further promoted when ultraviolet (UV) light damage can be eliminated. However, there is no safe and effective product in the market that can simultaneously enhance the secretion of collagen, prevent glycation of collagen, and resist UV light damage available in the market, particularly, food products, for an all-inclusive protection and prevention of cutaneous aging.

SUMMARY OF THE INVENTION

As a result, the present invention provides a method for enhancing collagen secretion of skin comprising topologically applying or orally administrating to a subject a composition containing, as active ingredient, a *Chenopodium formosanum* extract, wherein the *Chenopodium formosanum* extract is obtained by solvent extraction of the *Chenopodium formosanum*. In one embodiment of the present invention, the *Chenopodium formosanum* is whole grain (un-dehulled) *Chenopodium formosanum* and/or dehulled *Chenopodium formosanum*. The collagen is a connective tissue collagen.

In one embodiment of the present invention, the solvent comprises water, alcohol, and acid. The solvent extraction is performed in a *Chenopodium formosanum* to solvent ratio of 1:7 to 1:10 (w/v) and at a temperature of 25° C. to 70° C. The *Chenopodium formosanum* extract obtained has, preferably, a polyphenol content of 70 to 340 μg/L and a flavonoid content of 80 to 430 μg/L.

Another aspect of the present invention is to provide a method for ameliorating cutaneous aging in a subject in need thereof, comprising orally administrating or topologically applying a composition having an active amount of *Chenopodium formosanum* extract to the subject in need thereof, wherein the *Chenopodium formosanum* extract is obtained by solvent extraction of the *Chenopodium formosanum*. In one embodiment of the present invention, the solvent comprises water, alcohol, and acid. The solvent extraction is performed in a *Chenopodium formosanum* to solvent ratio of 1:7 to 1:10 (w/v) and at a temperature of 25° C. to 70° C. The *Chenopodium formosanum* extract obtained has, preferably, a polyphenol content of 70 to 340 µg/L and a flavonoid content of 80 to 430 µg/L.

In one embodiment of the present invention, the *Chenopodium formosanum* extract suppress the glycation of collagen. In another embodiment of the present invention, the *Chenopodium formosanum* extract reduce the cell damage caused by ultraviolet light, wherein the *Chenopodium formosanum* extract increase the cell viability of a cell upon exposure to ultraviolet light and the cell is a dermal fibroblast. The composition of the present invention ameliorates cutaneous photoaging as well as nurses, and/or improves skin conditions. The composition of the present invention is an external embrocation, an external medicament, an external skin care product, a cosmetic product, a food product or a health supplement.

The *Chenopodium formosanum* extract of the present invention contains several active ingredients, such as polyphenols, flavonoids, and saponins, etc, and are mainly betacyanin, betaxanthin, and saponin. The applicant proved, via experimentation, that the *Chenopodium formosanum* extract of the present invention can significantly enhance the collagen secretion rate of the dermal fibroblasts and can effectively prevent the glycation of collagen as well as resist to UV light damage. The *Chenopodium formosanum* extract of the present invention is obtained from a natural source by a simple, cost-effective, and environmental-friendly procedure. Thus, the *Chenopodium formosanum* extract of the present invention can be readily used in food or cosmetic products for amelioration of cutaneous aging and protection of skin.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

The *Chenopodium formosanum* extract of the present invention was prepared using a mild and easy procedure and was analyzed according to the active ingredients therein. In addition, the *Chenopodium formosanum* extract of the present invention was co-incubated with human dermal fibroblasts to verify its ability to enhance the secretion of collagen of the human dermal fibroblasts and the viability of human dermal fibroblasts under UV light exposure. On the other hand, since glycation of collagen would result in unwanted conditions such as decrease of skin moisture, skin unevenness, collagen breakdown, and abnormal cell morphologies, the *Chenopodium formosanum* extract of the present invention was also incubated with porcine collagen to show that the *Chenopodium formosanum* extract of the present invention can effectively suppress glycation of collagen. That is to say, in the presence of reducing sugar, the *Chenopodium formosanum* extract of the present invention can significantly reduce the glycation of collagen.

Definition

As used herein, the term "anti-aging" refers to the measure of preventing or ameliorating the aging appearances of human skin. Evaluation of achieving this purpose will depend on a number of factors known to those having ordinary skill in the art such as the general state, age, gender, etc, of the consumer. The anti-aging effect includes but not limit to enhancing collagen secretion, suppressing glycation of collagen, and resisting UV light damage.

As used herein, the term "photoaging" or "photoaging effect" refer to the aging phenomenon caused by ultraviolet (UV) light, which includes but not limit to increase of matrix metalloproteinase (MMP) in the dermis via the phosphorylation of the mitogen-activated protein kinase (MAPK) pathway. The MMP can digest collagen resulting in decrease of collagen content in skin. UV light also promotes the formation of organic or inorganic reactive oxygen species (ROS) such as oxygen ion, peroxide, and free radicals causing the denaturation and dysfunction of collagen.

Method and Material

Preparation of the *Chenopodium formosanum* Extract

*Chenopodium formosanum* from Pingtung county, Taiwan, was gathered and stored as whole grain (un-dehulled) at 4° C. Please refer to FIG. 1 for the preparation of

Figure 1:
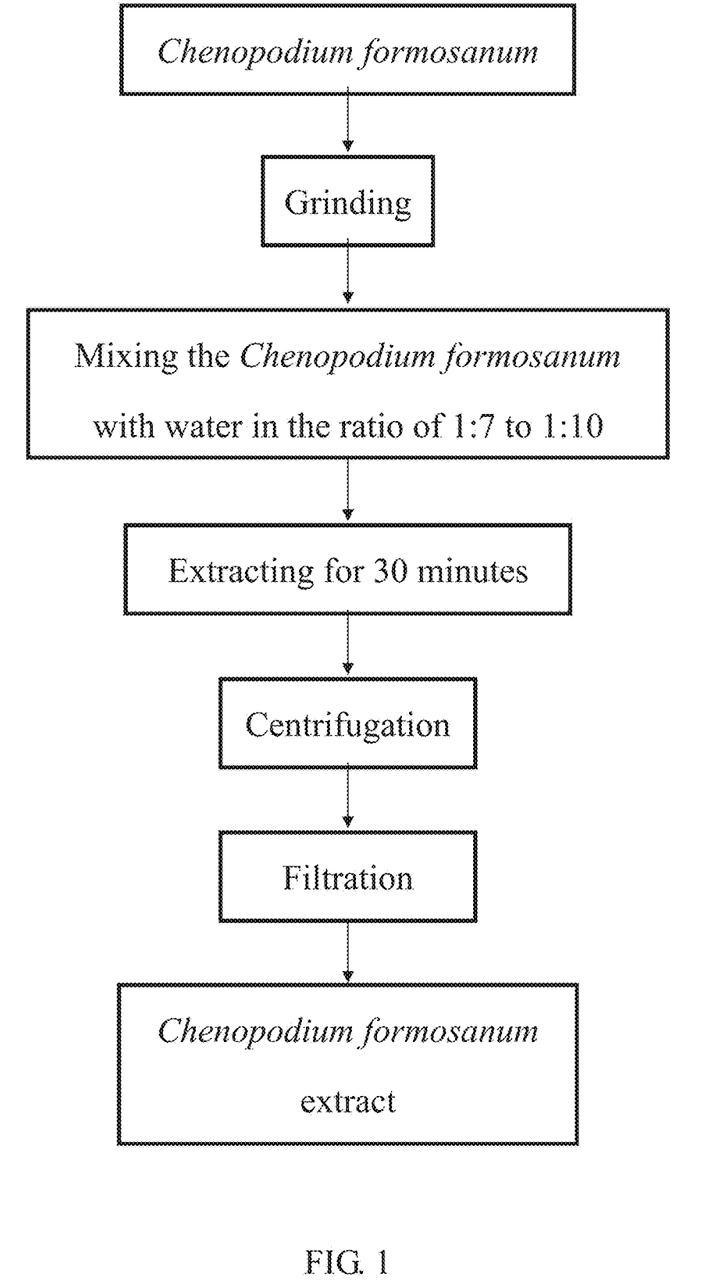
FIG. 1 is the flow chart of preparing the *Chenopodium formosanum* extract in accordance with one embodiment of the present invention.

*Chenopodium formosanum* extract. In order to maximize the outcome of extraction, *Chenopodium formosanum* can be transformed into smaller particles prior to extraction via physical methods such as pounding, grinding, and shattering, preferably grinding.

After extraction using solvent, the *Chenopodium formosanum* extract can be adjusted to various applications. However, for increasing the purity of the active ingredients in the *Chenopodium formosanum* extract, appropriate purification steps can be applied after the extraction procedure of the present invention. Said purification steps are known to a person having ordinary skill in the art and may include chromatography, crystallization, filtration, or precipitation, etc, according to practical requirements.

In one preferred embodiment of the present invention, 2.5 g of grinded *Chenopodium formosanum* was dissolved in 25 mL of water to form a mixture. The mixture was then extracted using water for 30 minutes under different temperatures. The *Chenopodium formosanum* used herein can be dehulled or whole grain (un-dehulled) *Chenopodium formosanum*. The ratio of the *Chenopodium formosanum* to water is 1:10 (w/v) and the temperatures are 25° C., 50° C., or 70° C. The extracted mixture was then centrifuged for 20 minutes at 4600 rpm to separate solid components. Finally, the centrifuged mixture was filtered and the supernatant thereof was collected to give the *Chenopodium formosanum* of the present invention.

On the other hand, sonication can also be utilized to obtain the *Chenopodium formosanum* extract of the present invention in larger quantity. The *Chenopodium formosanum* was grinded and extracted via sonication at the ratio of *Chenopodium formosanum* to water=1:7~1:10 (w/v) under 25° C. followed by centrifugation and filtration to remove solid components. The *Chenopodium formosanum* of the present invention was thus obtained after ultra-high-temperature sterilization. The *Chenopodium formosanum* extract from either preparation procedures was stored in sealed containers under 4° C.

Analysis of the Active Ingredients of the *Chenopodium formosanum* Extract

The concentrations of total phenol in the *Chenopodium formosanum* extract of the present invention are determined based on the Folin-Ciocalteu colorimetric method. The assay was performed as follows: 4 mL of 2% $Na_2CO_3$ and 5 mL of Folin-Ciocalteau reagent were added to 1 mL of *Chenopodium formosanum* extract or standard solution in test tubes for reaction. Gallic acid was used as the standard solution at concentration from 200 to 1000 ppm. After 30 minutes of incubation at 25° C. in the dark, the absorbance of each sample was measured at 750 nm Please refer to Table 1 for the total phenol content of the *Chenopodium formosanum* extract of the present invention.

The total flavonoid content of the *Chenopodium formosanum* extract of the present invention was analyzed by the aluminum chloride colorimetric assay. 1 mL of the *Chenopodium formosanum* extract of the present invention or standard solution and 1 mL of 5% $NaNO_2$ were added to 10 mL volumetric flask containing 4 mL of $dH_2O$. The standard solution was made of rutin at the concentration from 8 to 48 ppm. After 6 minutes, 1 mL of 10% $AlCl_3$ was added to the flask. After another 6 minutes, 10 mL of 4% NaOH was added and the total volume was made up to 25 mL with $dH_2O$. The solution was well-mixed and the absorbance was measured at 500 nm. Please also refer to Table 1 for the total flavonoid content of the *Chenopodium formosanum* extract of the present invention.

TABLE 1

| | Temperature of extraction (° C.) | Total flavonoid content (µg of rutin/mL) | Standard deviation | Total phenol content (µg of gallic acid/mL) | Standard deviation |
|---|---|---|---|---|---|
| Whole grain (Un-dehulled) *Chenopodium formosanum* | 25° C. | 418 | 14 | 326 | 26 |
| | 50° C. | 418 | 4 | 332 | 18 |
| | 70° C. | 421 | 8 | 318 | 20 |
| Dehulled *Chenopodium formosanum* | 25° C. | 105 | 7 | 110 | 2 |
| | 50° C. | 116 | 9 | 90 | 18 |
| | 70° C. | 87 | 9 | 73 | 11 |

Example 1

Analysis of the Ability to Promote Collagen Secretion of the *Chenopodium Formosanum* Extract Firstly, human dermal fibroblasts (CCD-966SK) were seeded at an initial concentration of $4\times10^4$ cells per well on a 24-well plate in MEM containing 10% of FBS. After 24 hours of incubation, the culture medium was replaced by fresh medium. The *Chenopodium formosanum* extract was diluted into a concentration of 0.2 mg/mL with phosphate buffer saline (PBS) to be added into each well. Cells without the treatment of *Chenopodium formosanum* extract served as the control group. After incubation for 48 hours at 37° C. with 5% $CO_2$, the supernatants were collected. The total amount of soluble type I collagen was assayed using the Sircol® Collagen Assay Kit (Bicolor Life Science Assays, Northern Ireland, UK). 100 µL of supernatant obtain from the above method was mixed with 1 mL of Sircol® dye solution at room temperature for 30 minutes. Then, centrifugation of 15,000×g was applied for 10 minutes to form collagen pellets. The supernatant was removed after the centrifugation and the produced soluble collagen was dissolved in 1 mL of alkali reagent. The resultant alkali reagent solutions were assayed by a spectrophotometer at a wavelength of 540 nm. The amount of collagen was calculated based on a standard curve of soluble collagen.

Figure 2A:
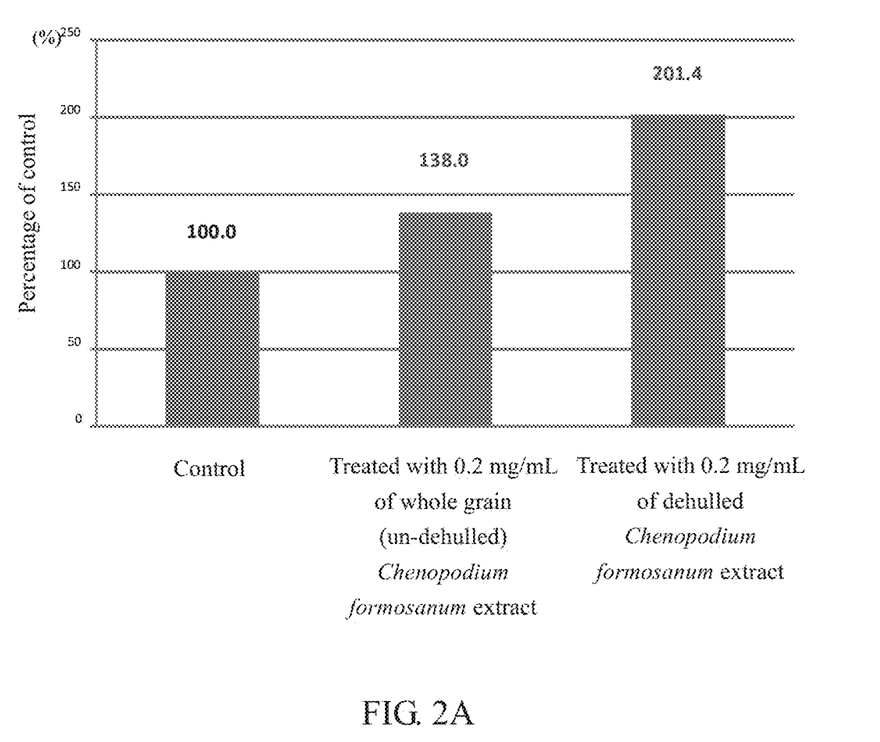
FIG. 2A illustrates the ability to enhance collagen secretion of the *Chenopodium formosanum* extract in accordance with one embodiment of the present invention.

The results for the ability of the *Chenopodium formosanum* extract of the present invention to enhance collagen secretion rate are shown in FIG. 2A, wherein, in FIG. 2A, the vertical axis represents the percentage of collagen secretion rate based on the control group being 100%. It is found that when treated by 0.2 mg/mL of whole grain (un-dehulled) *Chenopodium formosanum* extract, the collagen secretion rate of the human dermal fibroblasts is 138%, showing a 38% increase comparing to the control group; when treated by 0.2 mg/mL of dehulled *Chenopodium formosanum* extract, the collagen secretion rate of the human dermal fibroblasts reaches 201.4%, which is approximately 2 times greater than the control group. Therefore, both dehulled and whole grain (un-dehulled) *Chenopodium formosanum* extract of the present invention are proven to be able to effectively enhance the collagen secretion rate of cells.

Figure 2B:
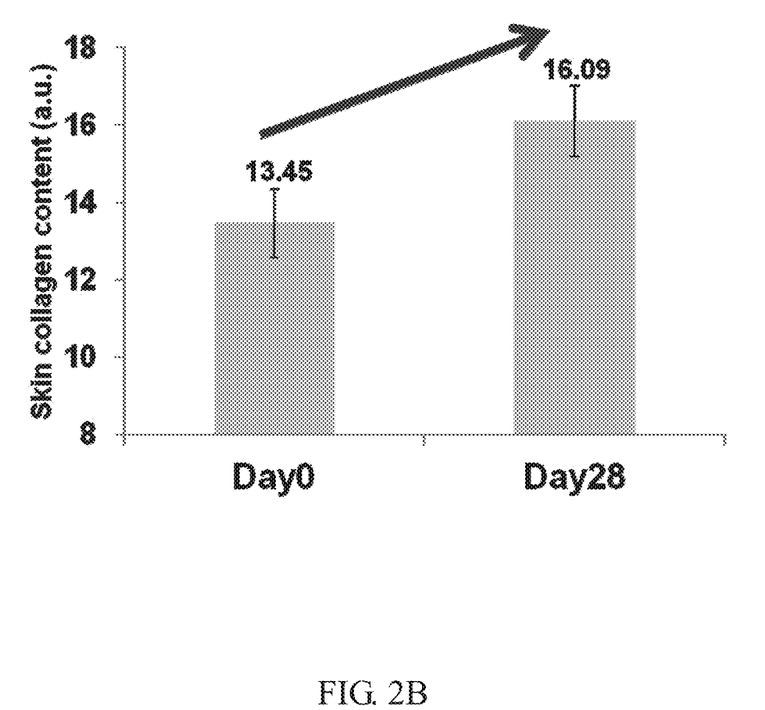
FIG. 2B illustrates the ability to promote collagen content in skin of the *Chenopodium formosanum* extract in accordance with one embodiment of the present invention.
Figure 2C:
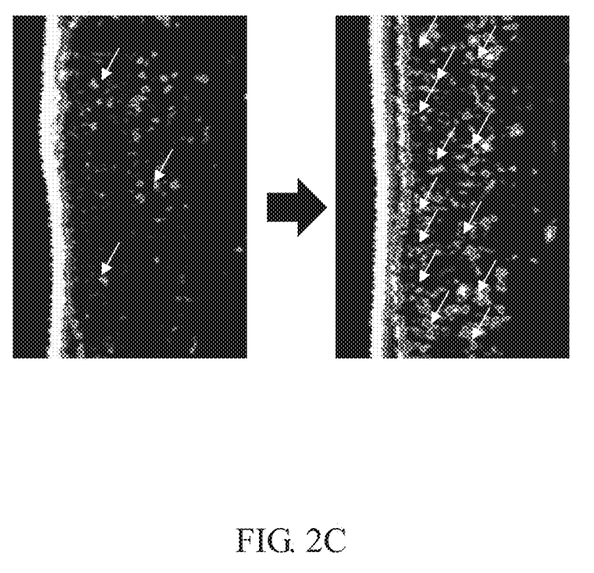
FIG. 2C is the fluorescence dyed microscopic image of the *Chenopodium formosanum* extract of the present invention for promoting collagen content in skin, wherein the image on the left indicates the collagen content in skin before the intake of the *Chenopodium formosanum* extract of the present invention; the image on the right indicates the collagen content in skin after the intake of the *Chenopodium formosanum* extract in accordance with one embodiment of the present invention for 28 days.

The effect of the *Chenopodium formosanum* extract of the present invention regarding promoting collagen content in skin during clinical test is shown in FIG. 2B and FIG. 2C. For clinical test, 11 adults (male:female=2:9) of age range from 25 to 40 (average age: 30) were arranged to take the *Chenopodium formosanum* extract of the present invention orally in the dosage of 5 mL per day for 28 days. As shown in FIG. 2B, the collagen content in skin after continuous intake of the *Chenopodium formosanum* extract of the present invention according to the above dosage for 28 days increases 19.6% comparing to the collagen content in skin at day 0. As shown in FIG. 2C, the collagen content in skin (illustrated as white arrows) after continuous intake of the *Chenopodium formosanum* extract of the present invention according to the above dosage for 28 days (image on the right) significantly increases comparing to the collagen content in skin (illustrated as white arrows) before the intake of the *Chenopodium formosanum* extract of the present invention. Thus, though clinical test, the intake of the *Chenopodium formosanum* extract of the present invention can effectively increase the collagen content in skin.

Example 2

Analysis of the Ability to Prevent Glycation of Collagen of the *Chenopodium Formosanum* Extract In order to evaluate the ability to prevent glycation of collagen of the *Chenopodium formosanum* extract, firstly, porcine collagen (60 mg/mL) and fructose (1.5 M) were respectively prepared in 0.2 M potassium phosphate buffer (pH 7.4, containing 0.06% sodium azide). For each reaction of glycation, 100 μL of porcine collagen, 100 μL of fructose solution, and 100 μL of deionized water were deposited in a 1.5 mL microfuge tube. After incubation, the reacted solutions were stored frozen at −20° C. For determination of collagen-fructose glycation, a glycation inhibitor of aminoguanidine (AG) (Sigma) was used. 100 μL of 3 mM AG solution (prepared in deionized water) was introduced in substitution of the deionized water in each of the reactions described above containing collagen and fructose. Meanwhile, different concentrations of the whole grain (un-dehulled) *Chenopodium formosanum* extract were also prepared and introduced to the reactions describe above. For determination of the intensity, 100 μL of each reacted solution was withdrawn to a well of a 96-well plate and subjected to intensity determination by a spectrofluorometer (FLx 800, BioTek, Winooski, Vt.) set at 360 nm of excitation and 460 nm of emission.

Figure 3A:
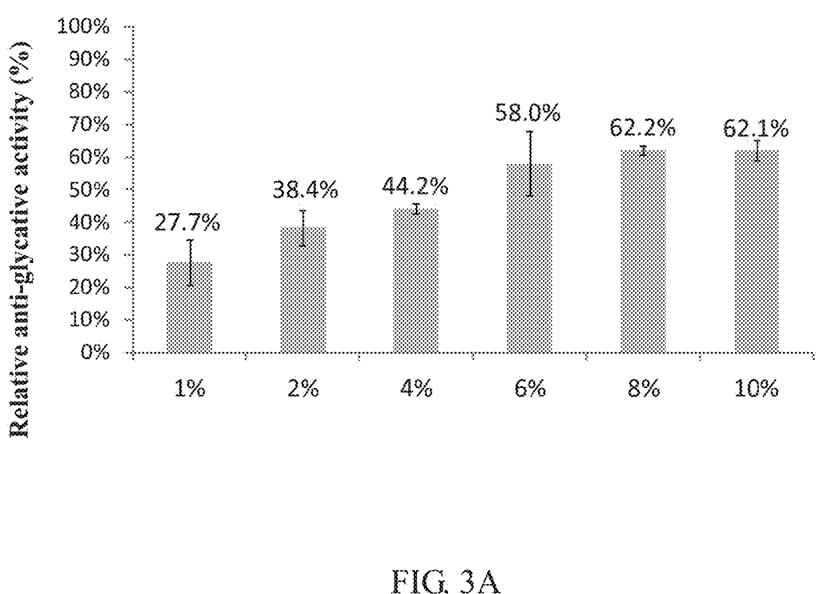
FIG. 3A illustrates the ability to suppress glycation of collagen of the *Chenopodium formosanum* extract in accordance with one embodiment of the present invention.

As shown in FIG. 3A, in general the *Chenopodium formosanum* extract of the present invention can suppress the glycation of collagen, wherein the suppression of glycation of collagen is maximized to 62.2% when 8% (w/w) of the whole grain (un-dehulled) *Chenopodium formosanum* extract was used. Experiments also show that the dehulled *Chenopodium formosanum* extract exhibit similar suppression of glycation of collagen (not shown).

Figure 3B:
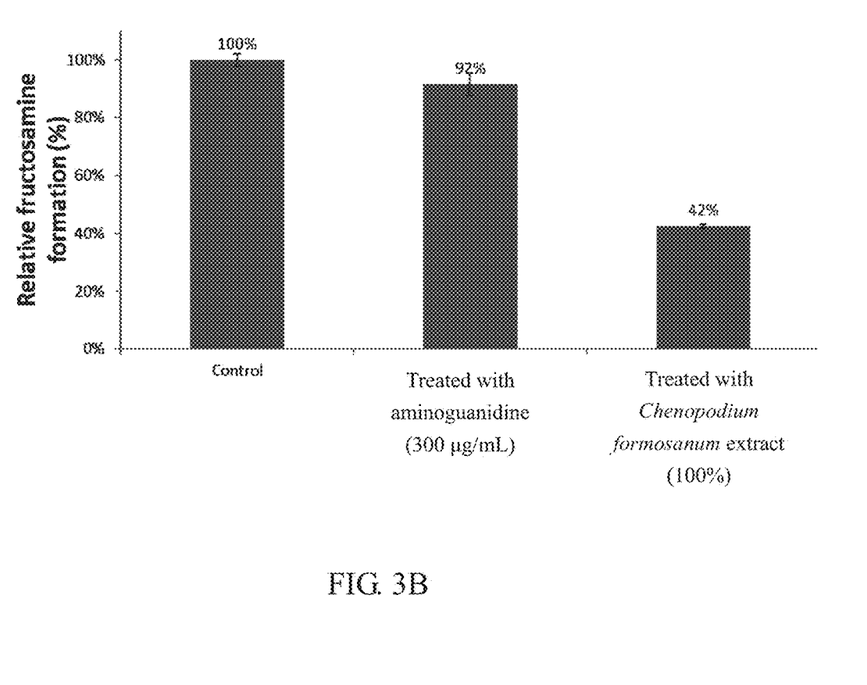
FIG. 3B illustrates the ability to reduce the formation of early glycation product of the *Chenopodium formosanum* extract.

Amadori product such as fructosamine is formed at the early stage of glycation. Collagen was glycated according to the aforementioned procedure, while collagen without the treatment of either aminoguanidine or the *Chenopodium formosanum* extract was set as the control group. As shown in FIG. 3B, when treated with the *Chenopodium formosanum* extract of the present invention, the relative fructosamine formation can be reduced up to 58%. This effect is significantly superior comparing with the treatment of aminoguanidine which only reduce the relative fructosamine formation about 8%.

Figure 3C:
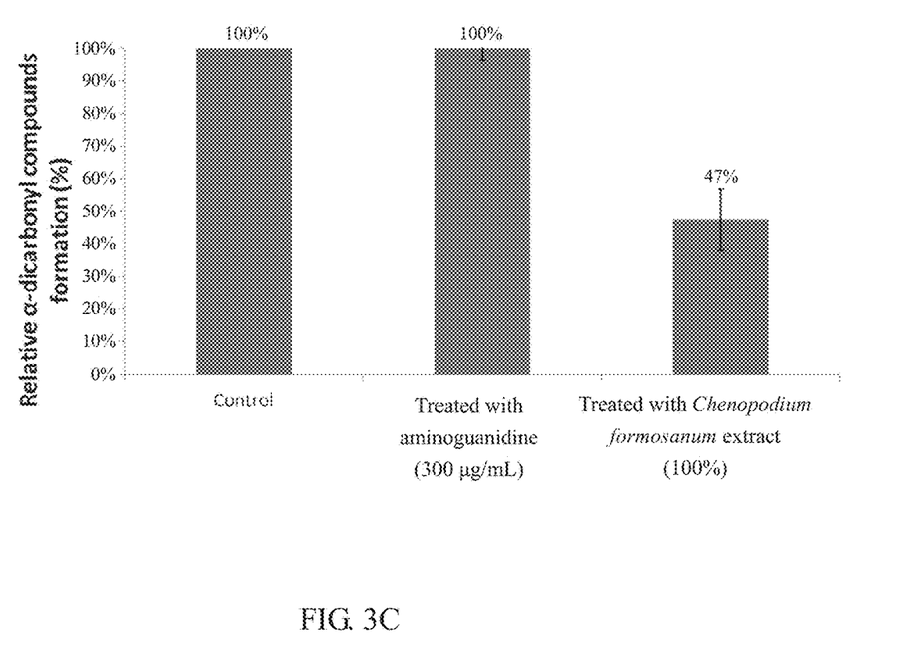
FIG. 3C illustrates the ability to reduce the formation of intermediate glycation product of the *Chenopodium formosanum* extract.

Along the glycation process, amadori product is transformed into intermediate-product such as α-dicarbonyl compounds. Collagen was glycated according to the aforementioned procedure, while collagen without the treatment of either aminoguanidine or the *Chenopodium formosanum* extract was set as the control group. As shown in FIG. 3C, when treated with the *Chenopodium formosanum* extract of the present invention, the relative α-dicarbonyl compounds formation can be reduced up to 53%. On the other hand, aminoguanidine is practically incapable of suppressing the formation of α-dicarbonyl compounds.

Figure 3D:
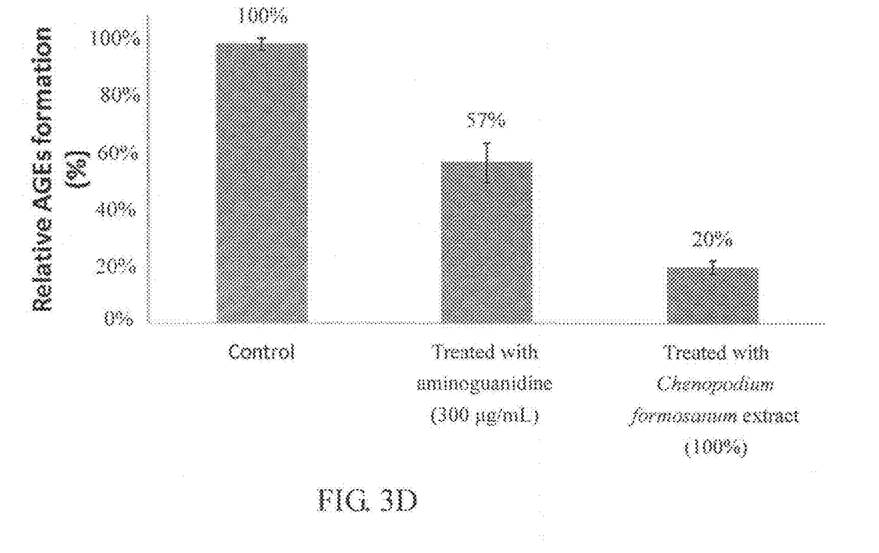
FIG. 3D illustrates the ability to reduce the formation of advanced glycation end-products of the *Chenopodium formosanum* extract.

Finally, during glycation, α-dicarbonyl compounds are transformed into advanced glycation end-products (AGEs). Collagen was glycated according to the aforementioned procedure, while collagen without the treatment of either aminoguanidine or the *Chenopodium formosanum* extract was set as the control group. As shown in FIG. 3D, the *Chenopodium formosanum* extract of the present invention exhibit significant inhibitory activity of AGEs that the AGEs formation is reduced up to 80%. Such inhibitory activity of the *Chenopodium formosanum* extract of the present invention is about twice greater than that of aminoguanidine.

Figure 3E:
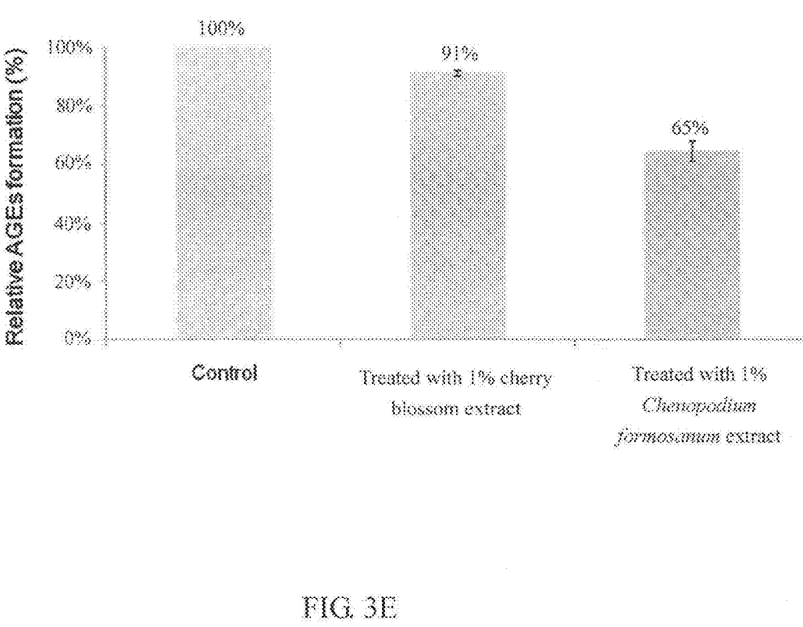
FIG. 3E is the comparison of the ability to reduce the formation of advanced glycation end-products of *Chenopodium formosanum* extract and cherry blossom extract.

In addition, although extract from other plant such as cherry blossom is known to the art as inhibitor for glycation of collagen as disclosed by, for instance, Hiroshi Shimoda, et al. in US 20130196937 A1, the *Chenopodium formosanum* extract of the present invention exhibit significantly competitive inhibitory ability regarding AGEs formation. Collagen was glycated according to the aforementioned procedure, while collagen without the treatment of either cherry blossom or *Chenopodium formosanum* extract was set as the control group. As shown in FIG. 3E, the treatment of 1% cherry blossom extract only reduce AGEs formation to 91%, whereas when collagen was treated by 1% *Chenopodium formosanum* extract of the present invention, the AGEs formation is reduced to 65%. That is to say, the inhibitory activity of the *Chenopodium formosanum* extract of the present invention is about 4 times greater than that of cherry blossom extract.

Example 3

Analysis of the Ability to Resist UV Light Damage of the *Chenopodium Formosanum* Extract Human dermal fibroblasts (CCD-966SK) were seeded at the concentration of $2 \times 10^4$ cells/well and were incubated for 24 hours at 37° C., 4% $CO_2$/96% air, followed by addition of 0.2 mg/mL of the whole grain (un-dehulled) or dehulled *Chenopodium formosanum* extract. The cells were then irradiated with 1.25 $J/cm^2$ of UVB (312 nm) or 15 $J/cm^2$ of UVA (365 nm). 3-(4,5-dimethylthiazol-2-yl)-2,5-diphenyltetrazolium bromide (MTT) was then added to the cells. After another 3 hours of incubation, the medium was withdrawn followed by addition of 100 μL dimethyl sulfoxide (DMSO) into each well. The UV source was positioned directly above the cell. The intensity at 540 nm was measured and cells without UV light exposure were used as control group.

Figure 4:
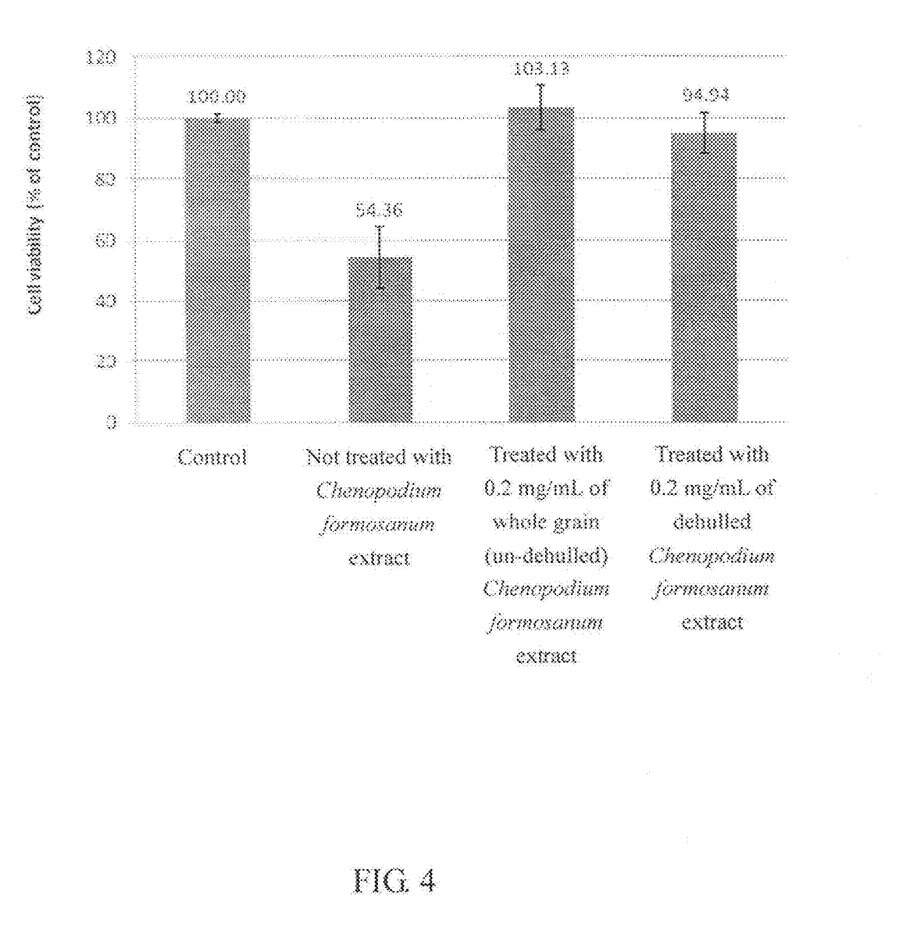
FIG. 4 illustrates the ability to promote cell viability under UV light exposure of the *Chenopodium formosanum* extract in accordance with one embodiment of the present invention.

As shown in FIG. 4, the cell viability of the control group, human dermal fibroblasts without UV light exposure, is 100%; after UV light exposure, the cell viabilities of the cells treated by the dehulled and whole grain (un-dehulled) *Chenopodium formosanum* extract are 94.94% and 103.13%, respectively. When comparing to the cell viability of the cells exposed to UV light but not treated by *Chenopodium formosanum* extract (54.36%), the treatment of *Chenopodium formosanum* extract increase the cell viability about 40 to 50%. It is thus proven that when treated by *Chenopodium formosanum* extract prior to UV light exposure, the cell viability of the human dermal fibroblasts is effectively promoted, indicating that the dehulled and whole grain (un-dehulled) *Chenopodium formosanum* extract of the present invention can both effectively prevent and lower the damage to cells caused by exposure to UV light.

Example 4

Use of *Chenopodium formosanum* Extract for the Manufacture of Food Products that Enhance Collagen Secretion and Ameliorate Cutaneous Aging The *Chenopodium formosanum* extract can be used for the manufacture of food products in the form of functional food or drinks, such as health supplements and beauty drinks. The addition of *Chenopodium formosanum* extract can promote the effect of collagen secretion and cutaneous aging amelioration of such products. As shown in Table 2, the *Chenopodium formosanum* extract of the present invention is introduced to the exemplary formulation of food products, specifically, drinks.

TABLE 2 formulation of drinks containing the *Chenopodium formosanum* extract

| Ingredients | % (w/w) |
|---|---|
| *Acacia* gum | 0.6-1 |
| *Chenopodium formosanum* extract | 10-20 |
| Citric acid | 0.2 |
| Liquid brown sugar (Flavor additive) | 0.01 |
| Concentrated apple juice | 6-8 |
| Fructose | 4-6 |
| Water | 64.79-79.19 |

Example 5

Use of *Chenopodium formosanum* Extract for the Manufacture of Cosmetic Products that Enhance Collagen Secretion and Ameliorate Cutaneous Aging The *Chenopodium formosanum* extract can be used for manufacture of cosmetic or skin care products in the form of solution, emulsion, cream, or gel, for external use. The addition of *Chenopodium formosanum* extract can promote the effect of collagen secretion and cutaneous aging amelioration of such products. As shown in Table 3, the *Chenopodium formosanum* extract of the present invention is introduced to the exemplary formulation of an essence.

TABLE 3 formulation of essence containing the *Chenopodium formosanum* extract

| Ingredients | % (w/w) |
|---|---|
| Water | 69.34-84.54 |
| Disodium EDTA | 0.03 |
| 1,3-butylene glycol | 5-10 |
| Methylisothiazolinone (preservative) | 0.08 |
| Glycerin | 5-10 |
| Dipotassium glycyrrhizinate | 0.1 |
| PEG-40 hydrogenated castor oil | 0.1-0.2 |
| *Chenopodium formosanum* extract | 5-10 |
| humectants | 0.05 |
| Glycosyl trehalose | 0.1-0.2 |

In summary, the *Chenopodium formosanum* extract of the present invention contains many active ingredients and is rich in flavonoids and polyphenols, thus, can effectively promote the collagen secretion rate of the dermal fibroblasts, suppress the glycation of collagen, and increase the cell viability of dermal fibroblasts when exposed to UV light. Moreover, the method of obtaining the *Chenopodium formosanum* extract of the present invention is simple and non-pollutant. Hence, the present invention not only effectively utilizes natural resources in a harmless way to the environment but also provides a highly-active and safe material for skin care and cosmetic products that ameliorate cutaneous aging.

The method for enhancing collagen secretion and preventing cutaneous aging using *Chenopodium formosanum* extract provided in present invention is applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. A method for enhancing collagen secretion of skin comprising topically applying or orally administrating to a subject an effective amount of a composition containing, as active ingredient, a *Chenopodium formosanum* extract, wherein the composition comprising the *Chenopodium formosanum* extract is continuously administered to the subject at a daily dosage of 5 mL for 28 days, wherein the extract is obtained by solvent extraction of the *Chenopodium formosanum*.

2. The method of claim 1, wherein the *Chenopodium formosanum* is whole grain *Chenopodium formosanum* and/or dehulled *Chenopodium formosanum*.

3. The method of claim 1, wherein the solvent comprises water, alcohol, and acid.

4. The method of claim 1, wherein the solvent extraction is performed in a *Chenopodium formosanum* to solvent ratio of 1:7 to 1:10 (w/v) and at a temperature of 25° C. to 70° C.; the *Chenopodium formosanum* extract obtained has a polyphenol content of 70 to 340 µg/L and a flavonoid content of 80 to 430 µg/L.

5. The method of claim 1, wherein the collagen is a connective tissue collagen.

6. A method for suppressing collagen glycation of skin in a subject in need thereof, comprising orally administrating or topically applying an effective amount of a composition having a *Chenopodium formosanum* extract to the subject in need thereof, wherein the composition comprising the *Chenopodium formosanum* extract is continuously administered to the subject at a daily dosage of 5 mL for 28 days, wherein the extract is obtained by solvent extraction of the *Chenopodium formosanum*.

7. The method of claim 6, wherein the solvent comprises water, alcohol, and acid.

8. The method of claim 6, wherein the solvent extraction is performed in a *Chenopodium formosanum* to solvent ratio of 1:7 to 1:10 (w/v) and at a temperature of 25° C. to 70° C.; the *Chenopodium formosanum* extract obtained has a polyphenol content of 70 to 340 µg/L and a flavonoid content of 80 to 430 µg/L.

9. The method of claim 1, wherein the composition ameliorates, nurses, and/or improves skin conditions.

10. The method of claim 6, wherein the composition ameliorates, nurses, and/or improves skin conditions.

11. The method of claim 1, wherein the composition is an external embrocation, an external medicament, an external skin care product, or a cosmetic product.

12. The method of claim 6, wherein the composition is an external embrocation, an external medicament, an external skin care product, or a cosmetic product.

13. The method of claim 1, wherein the composition is a food product or a health supplement.

14. The method of claim 6, wherein the composition is a food product or a health supplement.

\* \* \* \* \*